(12) United States Patent
Moulton

(10) Patent No.: US 7,694,403 B2
(45) Date of Patent: Apr. 13, 2010

(54) METHOD OF FORMING IV CATHETER AND NEEDLE ASSEMBLY

(75) Inventor: William G. Moulton, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 834 days.

(21) Appl. No.: 10/550,642

(22) PCT Filed: Mar. 24, 2004

(86) PCT No.: PCT/US2004/008899

§ 371 (c)(1),
(2), (4) Date: Jun. 23, 2006

(87) PCT Pub. No.: WO2004/087247

PCT Pub. Date: Oct. 14, 2004

(65) Prior Publication Data

US 2006/0264833 A1    Nov. 23, 2006

Related U.S. Application Data

(60) Provisional application No. 60/457,345, filed on Mar. 25, 2003.

(51) Int. Cl.
*B23P 25/00* (2006.01)
*A61M 5/178* (2006.01)

(52) U.S. Cl. .................... 29/458; 604/164.01

(58) Field of Classification Search ............... 29/469.5, 29/458, 505; 604/164.01, 523, 272, 533, 604/162
See application file for complete search history.

(56) References Cited

U.S. PATENT DOCUMENTS

2005/0080378 A1* 4/2005 Cindrich et al. ......... 604/164.01
2006/0264828 A1* 11/2006 Woehr et al. ............... 604/110

FOREIGN PATENT DOCUMENTS

WO    WO9924092    *   5/1999

\* cited by examiner

*Primary Examiner*—John C Hong
(74) *Attorney, Agent, or Firm*—Kinney & Lange, P.A.

(57) ABSTRACT

An IV catheter includes a catheter having a wall defining a lumen, a proximal end, and a distal end. An adapter has a proximal end, a distal end and an internal cavity. The adapter is in fluid communication with the catheter lumen. A septum is positioned within the adapter cavity at the adapter proximal end. An extension tube extends laterally from the adapter and is in fluid communication with adapter cavity. A tip shield has a distal end, a proximal end and an internal cavity. The tip shield is positioned adjacent adapter proximal end and coaxially aligned with adapter. A hub has a proximal portion, a distal portion and an internal cavity. The hub is positioned adjacent the tip shield proximal end and is aligned coaxially with the tip shield. A cannula has a wall defining a lumen, a beveled distal end, an aperture in the wall of said cannula near the cannula distal end and a proximal end in the shape of a hook. The cannula passes through and is coaxially aligned with the catheter, adapter, tip shield and hub.

15 Claims, 11 Drawing Sheets

METHOD OF FORMING IV CATHETER AND NEEDLE ASSEMBLY

This application claims the benefit of U.S. Provisional application Ser. No. 60/457,345, filed Mar. 25, 2003, and incorporated herein.

BACKGROUND OF THE INVENTION

The subject invention relates to an IV catheter and introducer needle assembly that includes a needle shield that will safely shield the sharp distal tip of the introducer needle after the needle has been used to insert the catheter into a patient. Specifically, aspects of the invention are related to a needle and hub assembly for use with a catheter and introducer assembly having a needle shield, as well as a method of manufacturing such a needle and hub assembly.

Catheters, particularly intravascular (IV) catheters, are used for infusing fluid, such as normal saline solution, various medicaments and total parenteral nutrition, into a patient, withdrawing blood from a patient or monitoring various parameters of the patient's vascular system. Peripheral IV catheters tend to be relatively short, and typically are on the order of about two inches or less in length. The most common type of IV catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter and thus facilitates insertion of the catheter into the blood vessel. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

In order to verify proper placement of the catheter in the blood vessel, the clinician confirms that there is flashback of blood in a flashback chamber. Once proper placement of the catheter into the blood vessel is confirmed, the clinician applies pressure to the blood vessel by pressing down on the patient's skin over the blood vessel distal of the introducer needle and the catheter. This finger pressure occludes or at least minimizes further blood flow through the introducer needle and the catheter. The clinician then withdraws the introducer needle, leaving the catheter in place, and attaches an appropriate device to the catheter. Such a device can include a fluid delivery device, a PRN, a deadender cap or a blood pressure monitoring probe. Once the introducer needle is withdrawn from the catheter, the introducer needle is a "blood contaminated sharp" and must be properly handled.

In recent years, there has been great concern over the contamination of clinicians with a patient's blood and a recognition that "blood contaminated sharps" must be disposed to avoid an accidental needle stick. This concern has arisen because of the advent of currently incurable and fatal diseases, such as Acquired Immunosuppressive Deficiency Syndrome ("AIDS"), which can be transmitted by the exchange of body fluids from an infected person to another person. Thus, contact with the body fluid of an AIDS infected person must be avoided. As noted above, if an introducer needle has been used to place a catheter in a blood vessel of an AIDS infected person, the introducer needle, via its sharp distal tip, is a vehicle for the transmission of the disease. Although clinicians are aware of the need to properly handle "blood contaminated sharps", unfortunately in certain medical environments, such as emergency situations or as a result of inattention or neglect, needlesticks with a contaminated introducer needle still occur.

As a result of the problem of accidental needlesticks by "blood contaminated sharps", various needle shields have been developed for use in conjunction with intravenous catheters. For example, needle shields have been designed to secure the tip of the needle within the shield after use, such as disclosed in U.S. Provisional Application Ser. No. 60/390,499 filed Jun. 20, 2002, Utility application Ser. No. 09/499,331, filed Feb. 4, 2000, U.S. Pat. No. 6,379,333, or U.S. Pat. No. 6,004,294, each incorporated herein by reference. Certain of these IV catheters with needle shields are operated by physically withdrawing the needle by hand through the catheter until the tip of the needle is within the shield. Specifically, the clinician grasps a hub attached to the needle and pulls it away from the catheter. Consequently, the operation of these intravenous catheters with needle shields depends, in part, on a sound connection between the needle hub and the needle. Generally, the needle hub-needle connection works for its intended purpose but could be improved in certain applications.

SUMMARY OF THE INVENTION

One aspect of an implementation of the invention provides a needle and hub assembly in which the needle is sealed to prevent fluid flow through the needle from its tip to its proximal end. The seal may be formed by crimping the needle cannula closed.

Another aspect of one implementation of the invention is to create a geometry on the proximal end of a needle cannula which provides a mechanical surface or interlock to enhance adhesive bonding to the needle hub and to seal the cannula, preventing fluid flow therethrough.

Another aspect of an implementation of the invention provides a hook-shaped end on the needle cannula that may be conveniently and effectively secured to the needle hub, distally such that the hook-shaped proximal end is disposed within a glue well in the needle hub. Glue is inserted into the glue well and cured with UV light.

Certain implementations of this aspect of the invention provide that the needle is lubricated.

Another aspect of the invention relates to a method of forming a hook-shaped crimp in a needle cannula.

Another aspect of the invention relates to a method of securing a needle to a needle hub.

In accord with one implementation of the invention, an IV catheter is provided including a catheter having a wall defining a lumen, a proximal end, and a distal end. An adapter has a proximal end, a distal end and an internal cavity. The adapter is in fluid communication with the catheter lumen. A septum is positioned within the adapter cavity at the adapter proximal end. An extension tube extends laterally from the adapter and is in fluid communication with adapter cavity. A tip shield has a distal end, a proximal end and an internal cavity. The tip shield is positioned adjacent adapter proximal end and coaxially aligned with adapter. A hub has a proximal portion, a distal portion and an internal cavity. The hub is positioned adjacent the tip shield proximal end and is aligned coaxially with the tip shield. A cannula has a wall defining a lumen, a beveled distal end, an aperture in the wall of said cannula near the cannula distal end and a proximal end in the shape of a hook. The cannula passes through and is coaxially aligned with the catheter, adapter, tip shield and hub.

Certain implementations of this aspect of the invention provide that the hook shape of the cannula proximal end has an internal radius and an external radius; the hook shape external diameter is about 0.10 inch; the internal radius is offset toward the cannula distal end; and the cannula lumen at the distal end is crimped close.

Another aspect of the invention is directed to a cannula including a wall defining a lumen, a beveled distal end, and a hook shape at the proximal end. Certain implementations of this aspect of the invention provide that the hook shape has an internal radius and an external radius; the external diameter is about 0.10 inch; the internal radius is offset toward the cannula distal end; and the lumen at the proximal end is crimped closed.

In accord with yet another aspect of the invention, a method is provided for forming a cannula having a hook shape. A cannula is provided having a wall defining a lumen, a proximal end and a distal end. A die and a crimp pin are also provided. The proximal end is positioned at the die. The cannula proximal end is depressed into the die with pressure from the crimp pin. Certain implementations of this aspect of the invention provide that the die has a diameter of about 0.10 inch; the crimp pin has a radius of about 0.030 inch; and the centerline of the crimp is offset from the die centerline.

In accord with another aspect of the invention, a method is provided for forming a needle including providing a cannula having a sharp distal end and a proximal end. The proximal end is crimped to seal the proximal end. Certain implementations of this aspect of the invention provide that the proximal end is formed into a hook shape; the steps of crimping and the step of forming the hook are performed virtually simultaneously; the crimp is formed by pressing a crimp pin onto the proximal end of the cannula; the crimp is formed by pressing the proximal end of the cannula into a die; and the crimp pin is pressed into the proximal end of the cannula as the proximal end of the cannula is pressed into the die.

In accord with another aspect of the invention, a method of forming a needle assembly is provided. Specifically, a cannula having a sharp distal end and a proximal end is crimped at the proximal end to seal the proximal end. The cannula is inserted into a needle hub such that the proximal end of the cannula is disposed in a glue well. Glue is inserted into the glue well. The glue is cured.

Certain implementations of this aspect of the invention provide that: the needle hub includes a neck having a profile substantially matching the profile of the cannula, and the step of inserting the cannula into the needle hub includes positioning the cannula in the neck in a snug fit; the proximal end is formed into a hook shape; the step of crimping and the step of forming the hook are performed virtually simultaneously; the crimp is formed by pressing a crimp pin onto the proximal end of the cannula; the crimp is formed by pressing the proximal end of the cannula into a die; the crimp pin is pressed into the proximal end of the cannula as the proximal end of the cannula is pressed into the die.

In accord with another aspect of the invention, a method is provided for forming a needle assembly. A needle cannula having a distal end and a proximal end is inserted into a needle hub. The proximal end of the needle cannula is extended beyond the needle hub. The proximal end of the needle cannula is crimped such that it is sealed and formed into a hook shape at the proximal end. The cannula is displaced. Crimping the needle comprises disposing the proximal end of the needle cannula along a crimping pad and moving a crimping tool towards the needle cannula such that the tool forces the cannula onto the pad; the crimping tool is a crimping pin, and the crimping pin is moved in a straight line towards the needle cannula; the crimping pin is moved exclusively in a direction perpendicular to the axis of the needle cannula; the crimping pin is moved in a direction at a selected angle with respect to the axis of the needle cannula; the crimping pin is displaced in an arcuate path toward the crimping pad; a groove is disposed in the crimping pad; the crimping pin deforms the needle cannula into the groove; the crimping pin moves with respect to the crimping pad in a path that is either in a direction perpendicular to the axis of the needle cannula, in a direction at a selected angle with respect to the axis of the needle cannula, arcuate toward the crimping pad or a combination of these paths; and the axis of the crimping pin is off set proximally with respect to the axis of the groove.

In accord with another aspect of the invention, an IV catheter is provided. A catheter has a wall defining a lumen, a proximal end, and a distal end. An adapter having a proximal end, a distal end and an internal cavity. The adapter is in fluid communication with the catheter lumen. A tip shield has a distal end, a proximal end and an internal cavity. The shield is operably engaged to the adapter. A hub has a proximal portion, a distal portion and an internal cavity. A cannula has a wall defining a lumen, a beveled distal end, an aperture in the wall of said cannula near the cannula distal end, and a proximal end including a mechanical interlock. The mechanical interlock is disposed within the internal cavity of the hub and the cannula passes coaxially through the catheter.

In accord with yet another aspect of the invention, a needle assembly is provided. A cannula defines a lumen and includes a beveled distal end and a proximal end having a mechanical interlock. A hub is disposed on the mechanical interlock. Certain implementations of this aspect of the invention provide that: the mechanical interlock is a hook-shaped member with an internal radius and an external radius; the hook shape has an external diameter is about 0.10 inch; the internal radius is offset toward the cannula distal end; and the lumen at the proximal end is crimped closed.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
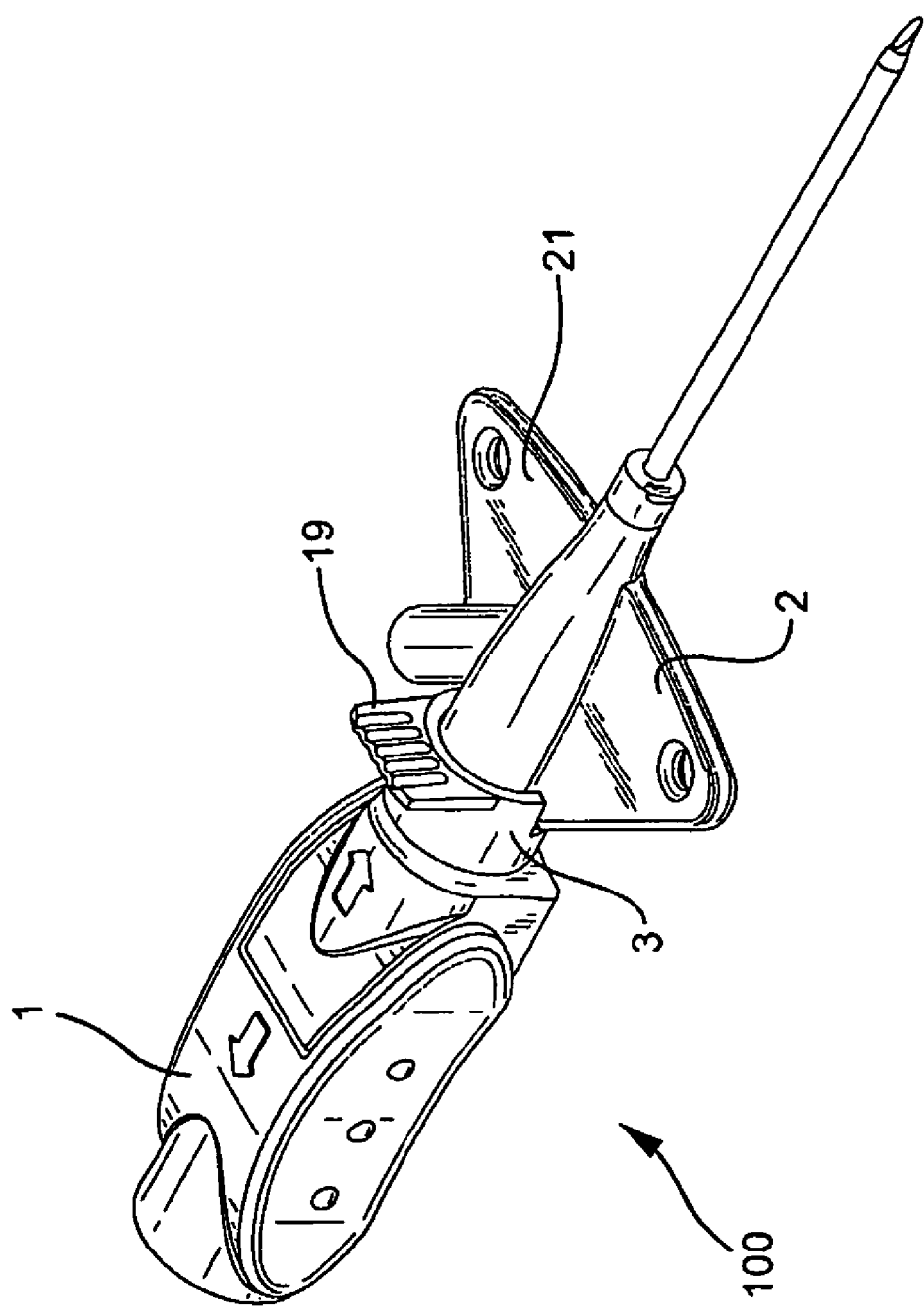
FIG. 1 is a perspective view of a catheter and introducer needle assembly used in conjunction with an aspect of the invention.
Figure 2:
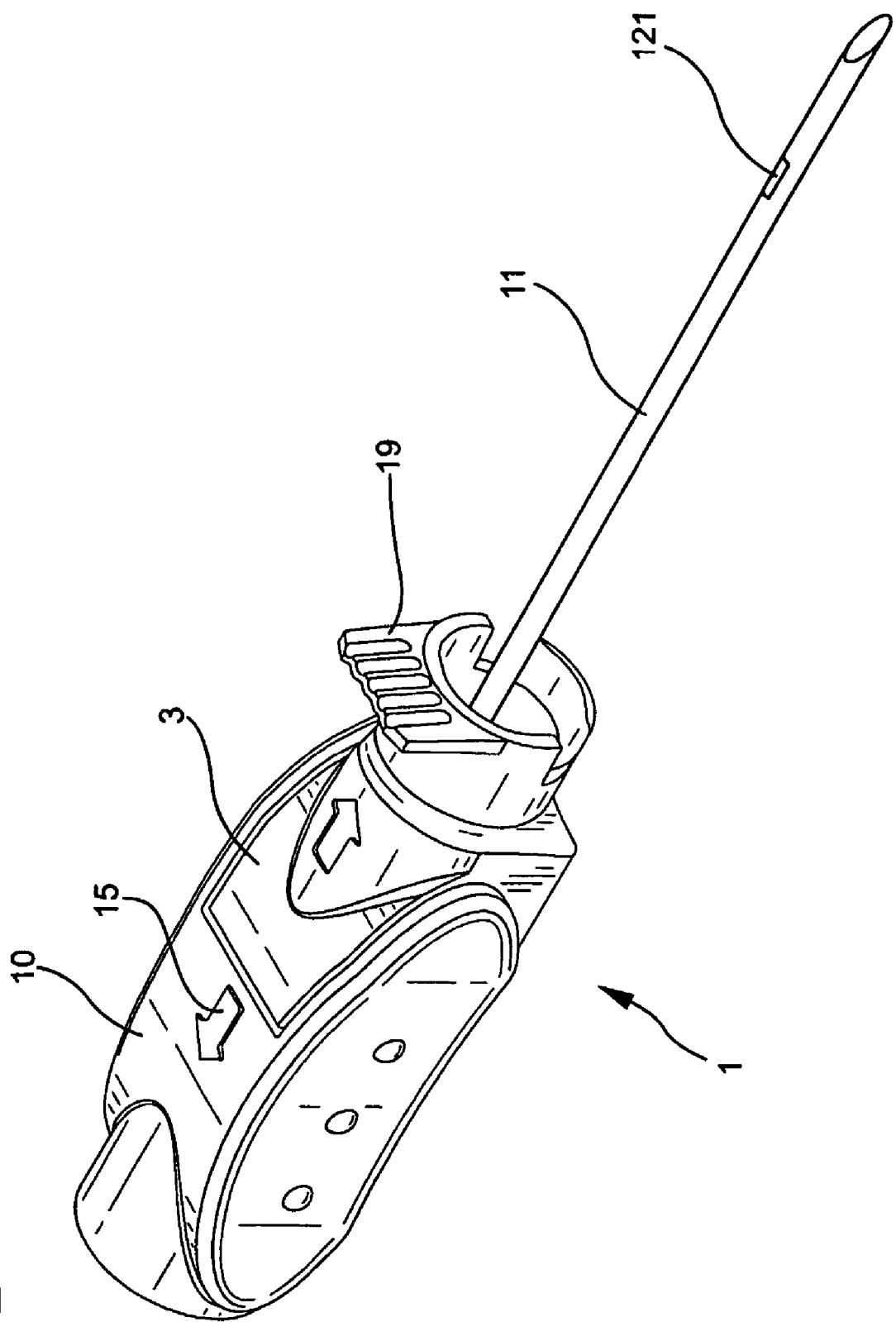
FIG. 2 is a front perspective view of a needle and hub assembly and needle shield in accord with an aspect of the invention.
Figure 3:
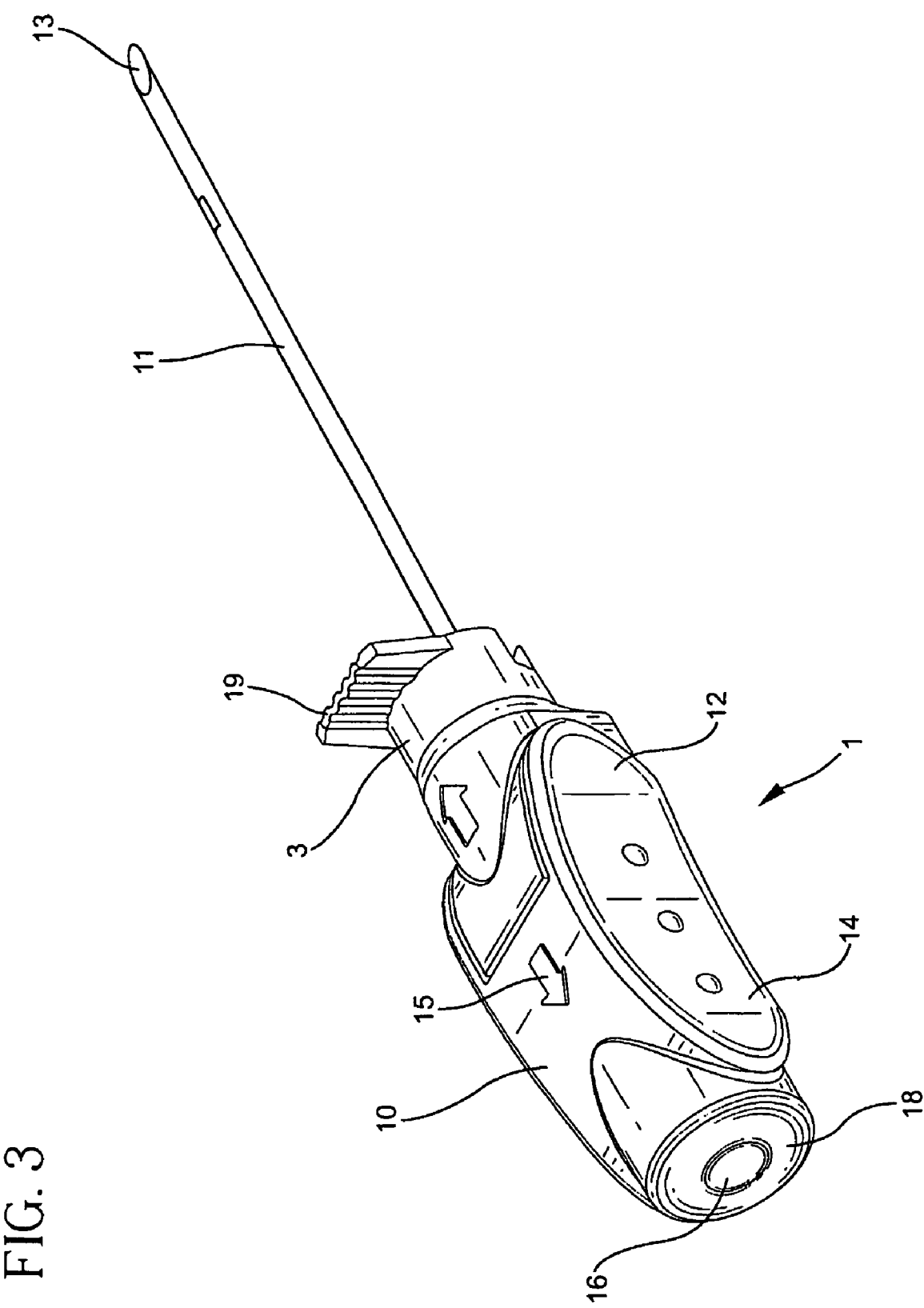
FIG. 3 is a rear perspective view of the needle and hub assembly and needle shield of FIG. 2.
Figure 4:
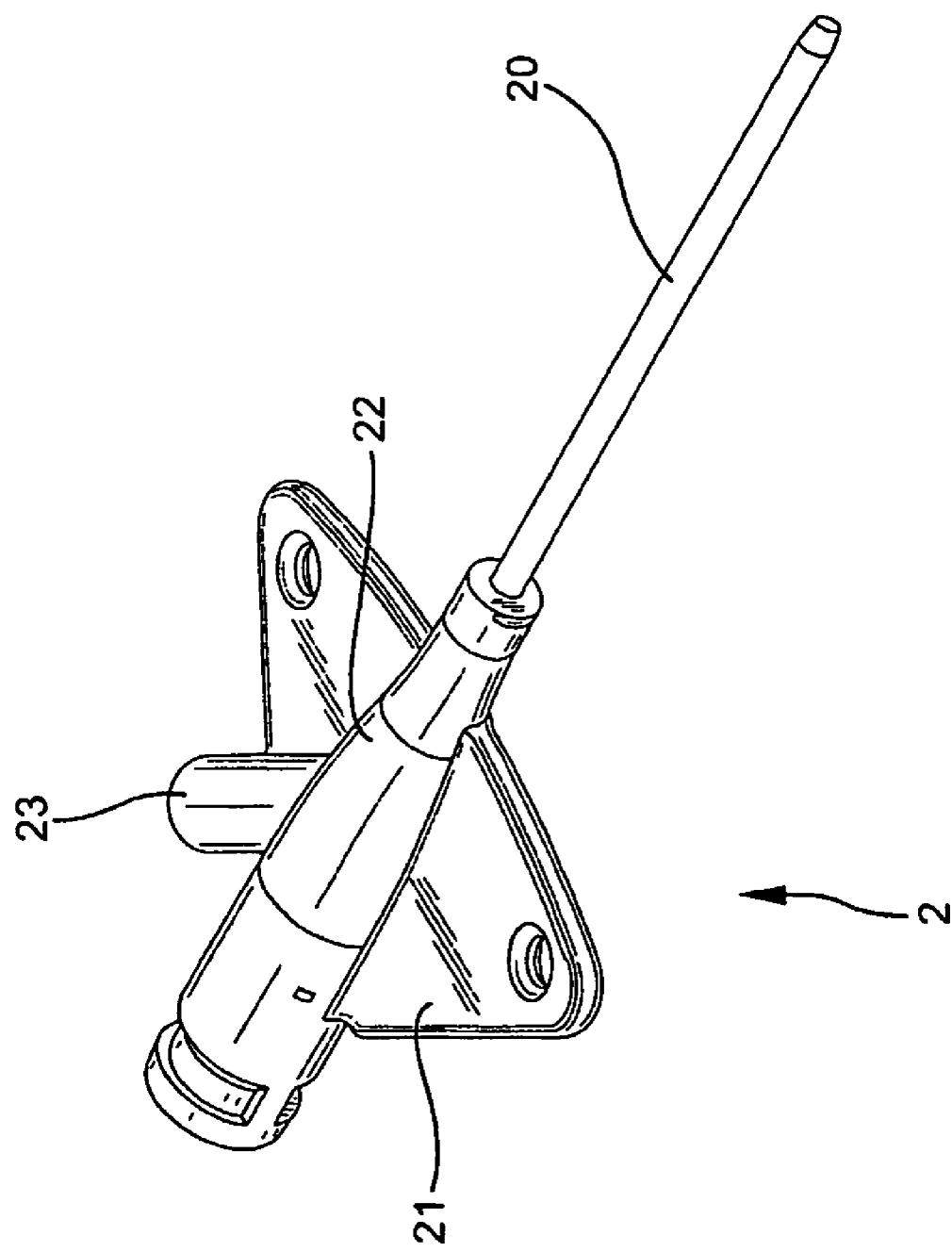
FIG. 4 is a perspective view of the catheter adapter for use in conjunction with the catheter and needle introducer assembly of FIG. 1.

As used herein, the term "proximal" refers to a location on the catheter and introducer needle assembly with the needle shield of this invention that, during normal use, is closest to the clinician using the device and farthest from the patient in connection with whom the device is used. Conversely, the term "distal" refers to a location on the catheter and introducer needle assembly of this invention that, during normal use, is farthest from the clinician using the device and closest to the patient in connection with whom the device is used.

As used herein, the term "top", "up" or "upwardly" refers to a location on the catheter and introducer needle assembly with the needle shield of this invention that, during normal use, is radially away from the longitudinal axis of the device and away from the patient's skin. Conversely, as used herein, the term "bottom", "down" or "downwardly" refers to a location on the catheter and introducer needle assembly with the needle shield of this invention that, during normal use, is radially away from the longitudinal axis of the device and toward the patient's skin.

As used herein, the term "in" or "inwardly" refers to a location with respect to the catheter and introducer needle assembly with the needle shield of this invention that, during normal use, is toward the inside of the device. Conversely, as used herein, the term "out" or "outwardly" refers to a location with respect to the catheter and introducer needle assembly with the needle shield of this invention that, during normal use, is toward the outside of the device.

Referring now to FIGS. 1-4, the needle hub 1 of the instant invention may be employed with a catheter and introducer assembly 100. The introducer assembly includes a needle hub assembly 1, a catheter adapter 2 and a needle shield 3. The needle shield may be a design adapted to secure the tip of the needle within the shield after use, such as disclosed in U.S. Provisional Application Ser. No. 60/390,499 filed Jun. 20, 2002, Utility application Ser. No. 09/499,331, filed Feb. 4, 2000, U.S. Pat. No. 6,379,333, or U.S. Pat. No. 6,004,294, each incorporated herein by reference.

The needle hub assembly 1 includes a hub body 10 having a needle cannula 11 extending from its distal end 12. The needle cannula itself includes a sharp distal tip 13 and a notch 121 disposed near the tip. The tip is adapted to be inserted into a patient's tissue, specifically, a patient's vein. As discussed below, a ferrule, crimp or other structure may be included near the tip for engagement with a needle shield in certain applications. Finger grips 14 are positioned at the sides of the hub 1. An arrow 15 (or other directional indicator) may be provided at the top of the needle hub to guide the caregiver. A thumb pad 16, having a gently convex surface, is provided at the proximal end of the hub. A glue well 17 having a substantially circular cross section provides a circular target 18 for the caregiver's thumb during use. A flange 19 of the shield 3 forms a finger pad. Further, wings 21 extend radially outwardly from the adapter body 22. The wings, finger pad and thumb pad way be employed by the caregiver during insertion, permitting the caregiver to elect which insertion technique to employ, as disclosed in U.S. Pat. No. 6,638,252, incorporated herein by reference.

As seen in FIG. 1, the needle extends coaxially through a catheter 20 of the catheter adapter when the introducer needle assembly 1 is assembled for use. A side port 23 extends from and is in fluid communication with the catheter adapter body 22. An extension tube may be attached to the side port to permit controlled flashback, as described in U.S. application Ser. No. 10/484,687, filed Jan. 23, 2004.

Figure 5:
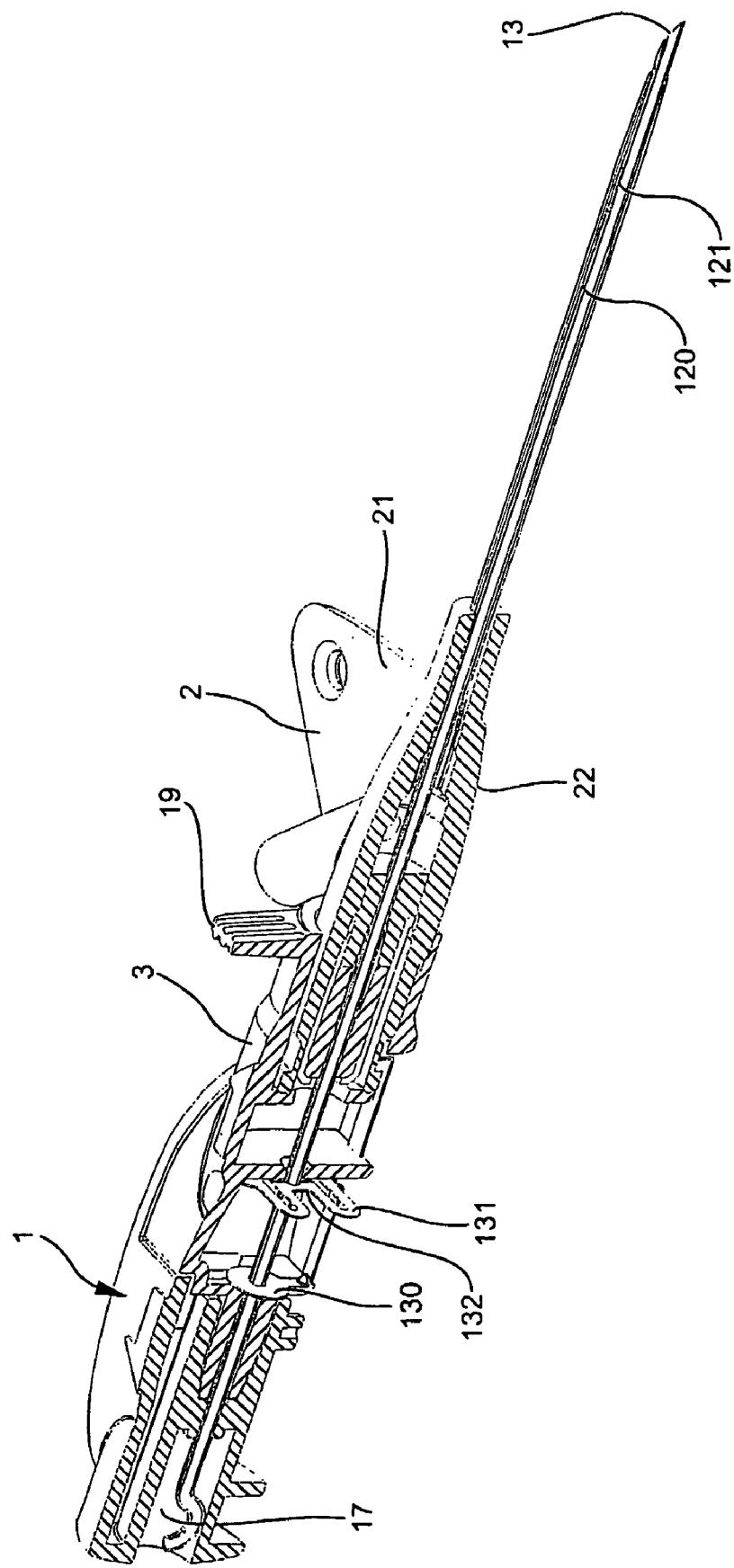
FIG. 5 is a perspective view, in cutaway, showing a catheter and introducer needle assembly used in conjunction with an aspect of the invention.
Figure 6:
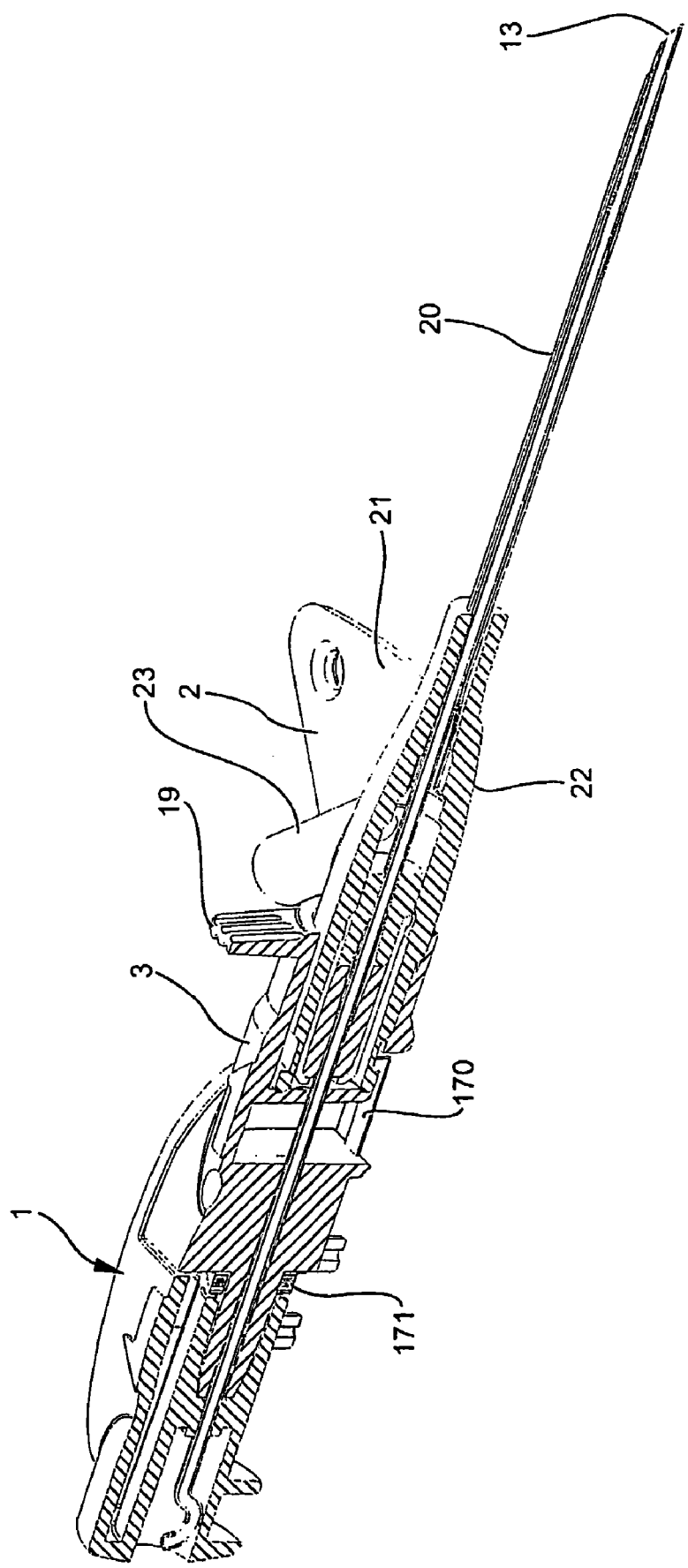
FIG. 6 is a perspective view, in cutaway, showing another catheter and introducer needle assembly used in conjunction with an aspect of the invention.
Figure 7:
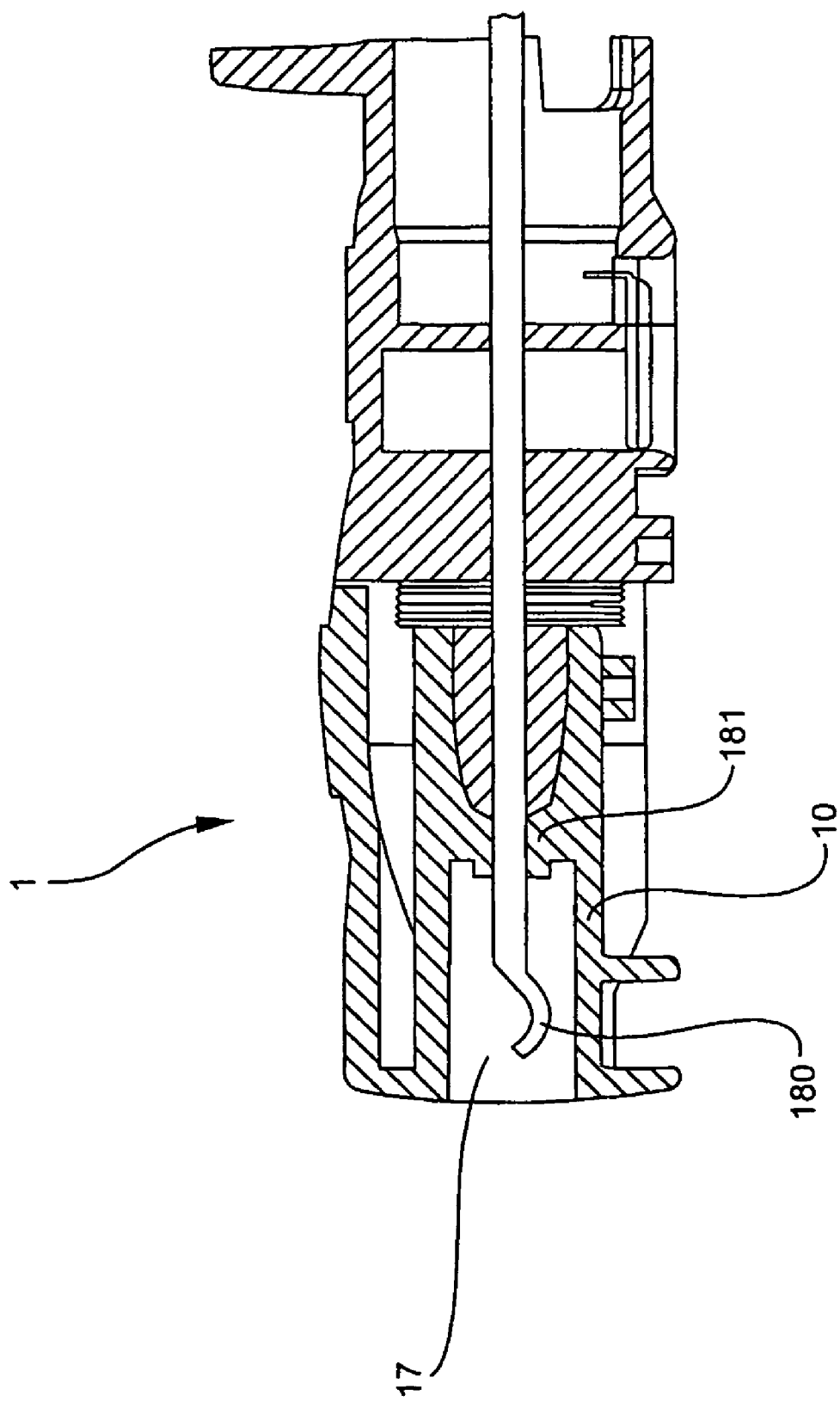
FIG. 7 is a cutaway view, in isolation, showing the needle hub in accord with an aspect of the invention.
Figure 8:
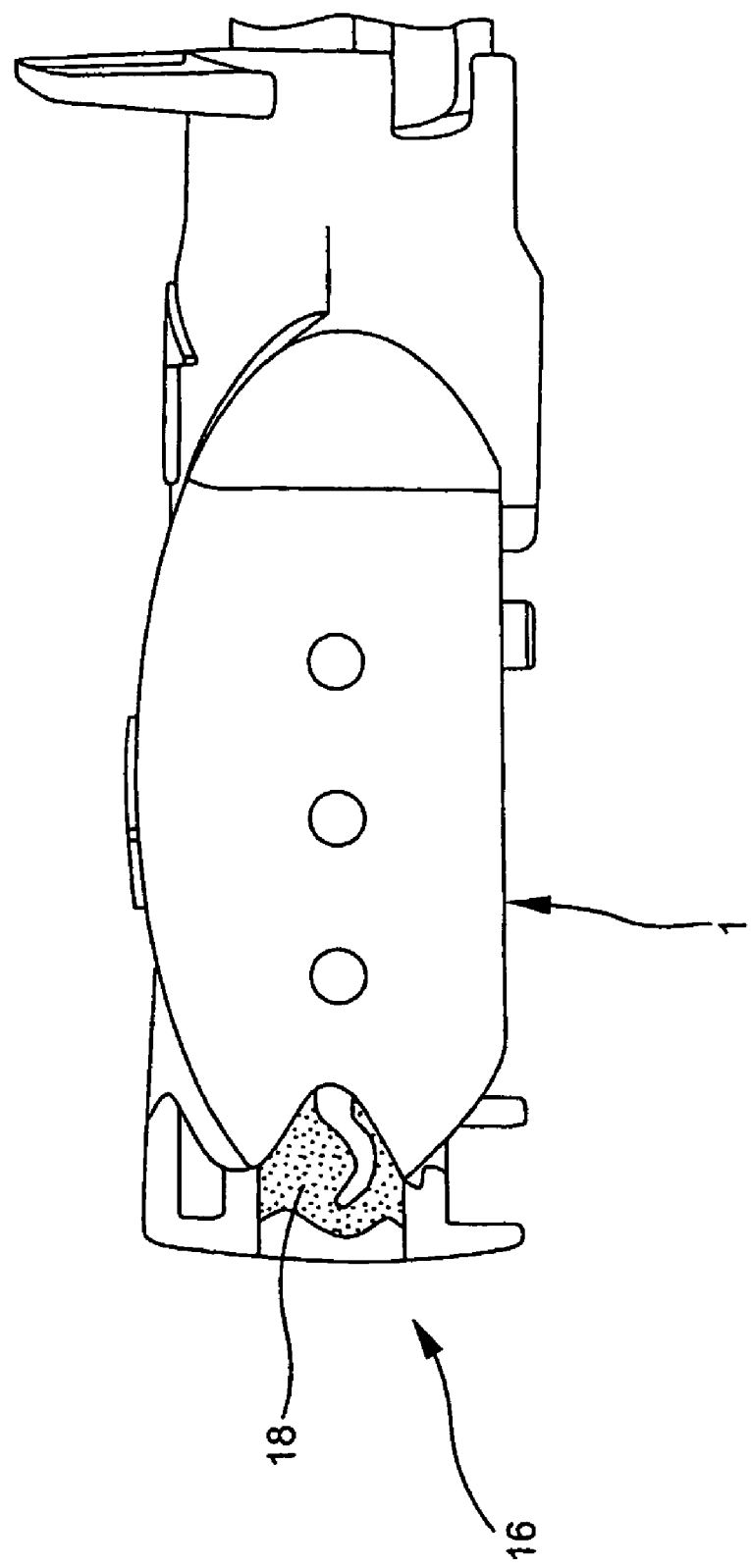
FIG. 8 is a partial cutaway view, in isolation, of the needle hub of FIG. 7.

Referring to FIG. 5, a first implementation of an aspect of the invention is depicted. The needle shield 3 includes a retention washer 130 and a retention plate 131. The retention plate includes two members 132 (only one shown). A sleeve or ferrule 120, or other structure, is provided near the tip 13 of the needle 11. Referring to FIG. 6, a second implementation of the invention is depicted. The needle shield 3 includes a clip 170 that prevents reemergence of the needle tip as it is withdrawn into the shield, and a tether 171 that prevents the shield from sliding off the tip of the needle. In both instances, and as shown in FIGS. 7 and 8, the proximal end 199 of the needle cannula 11 is crimped into a hook-shape 180, thereby sealing the proximal end of the cannula such that it is fluid tight. The hook-shaped end is disposed in a glue well 17 in the needle hub body 10. An adhesive 18 is delivered into the glue well and cured. The glue maintains the needle cannula firmly in place with respect to the needle hub, while ensuring that the proximal end of the needle cannula is sealed.

It will be appreciated that the hook 180 forms a mechanical interlock that allows the adhesive or glue to firmly grip the needle cannula 11. The gradual curvature of the hook prevents damage to the structural integrity of the cannula, such that it will not simply break. While a UV curable adhesive is desirable to secure the mechanical interlock to the needle hub, it will be appreciated that other structure can be employed and still practice aspects of the invention. For example, the neck 181 of the hub can be sized and shaped to engage the hook shaped member. Further, other types of adhesives may be employed.

Figure 9:
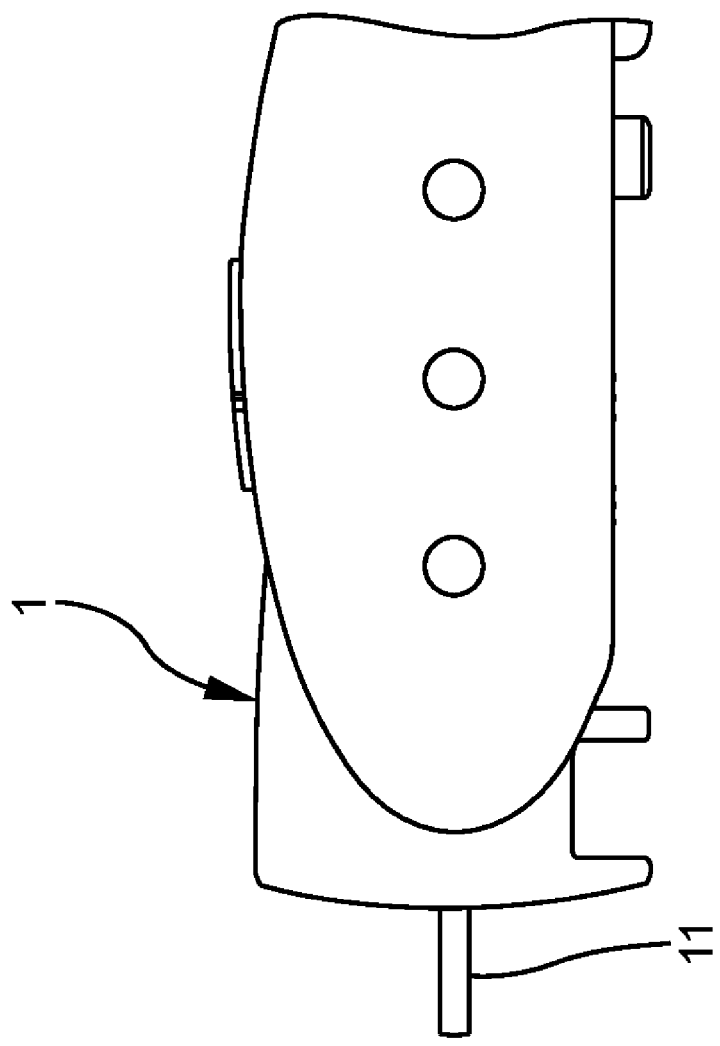
FIG. 9 is a side view, in isolation, showing the needle hub during assembly.
Figure 10:
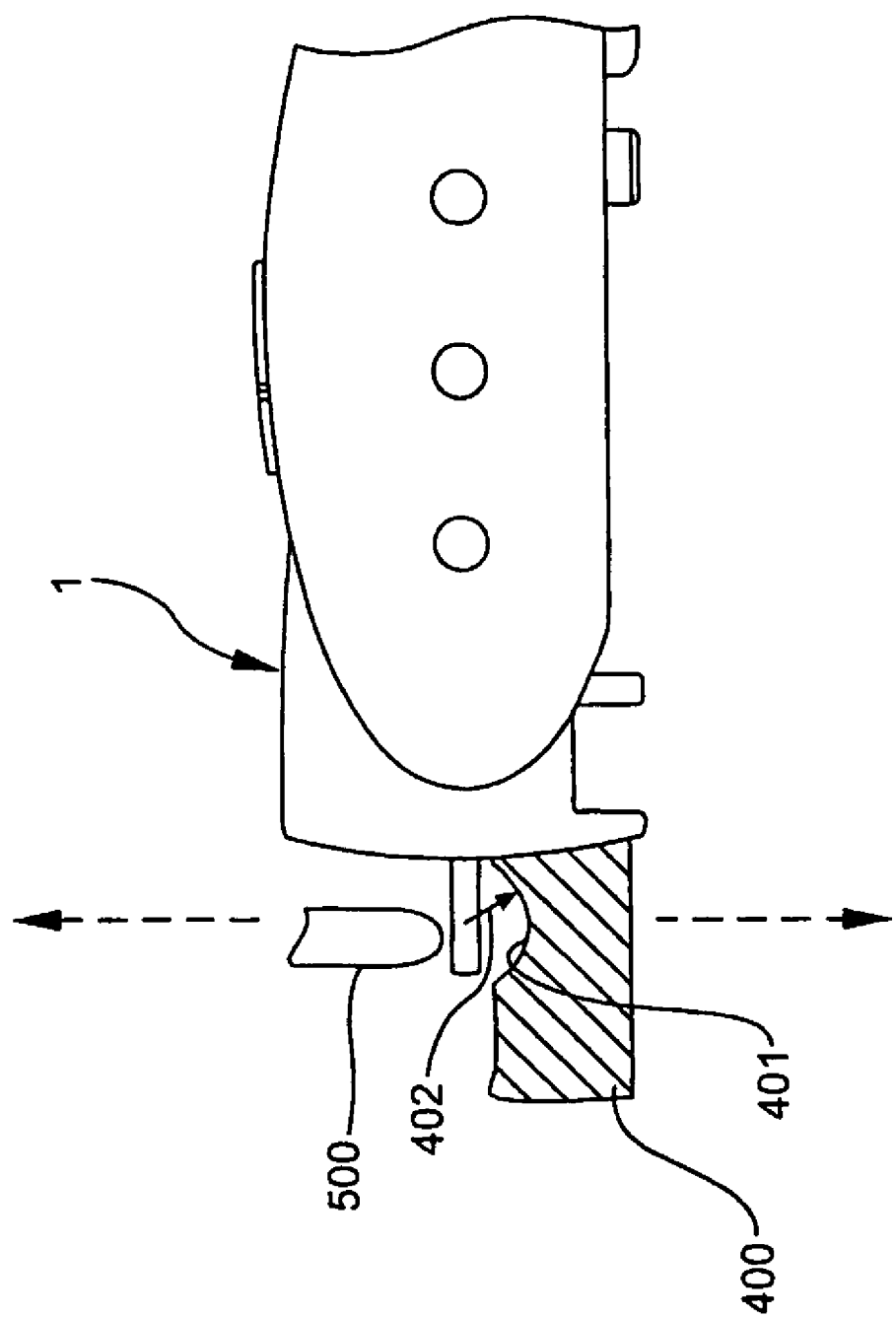
FIG. 10 is a side view showing the needle hub as the crimping process is beginning.
Figure 11:
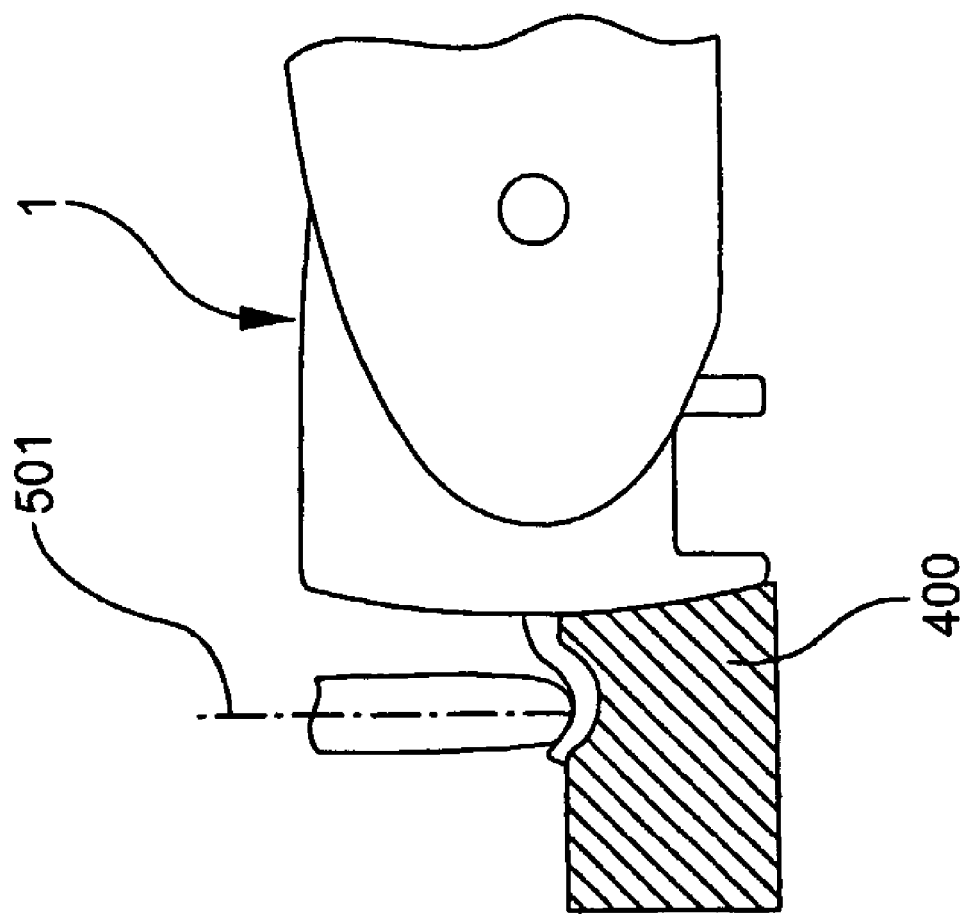
FIG. 11 is a side view showing the needle hub as the needle cannula is being crimped.

Referring now to FIGS. 9-11, the crimping operation will be described. The needle cannula 11 is inserted into the needle hub body 10 such that it is seated snugly in a neck portion 181 of the hub. The needle cannula may be lubricated before such insertion. While the cannula fits snugly within the neck, it can be slid within the neck. A selected length of the needle cannula at the proximal end 199 is extended proximally out of the needle hub, as seen in FIG. 9. It will be appreciated that this length can be adjusted depending on the particular implementation of the invention, based upon the crimping tool to be employed, the size of the glue well, the specific performance required of the crimped end, and so on.

The extended portion of the proximal end of the needle cannula is disposed over a crimp pad or die 400. The crimp pad includes a groove 401 having a pad radius 402. A crimp tool or crimp pin 500, having a tool radius, is disposed above the groove of the crimp pad. Preferably, the axis 501 of the crimp tool is displaced proximally with respect to the axis of the groove of the crimp pad. The motion of the crimp tool may be controlled, such that the crimp tool moves directly into the crimp pad, or at a selected angle into the crimp pad, or along a curved path into the crimp pad. A combination of these motions may be also be used. Different motions may be selected to achieve different crimps in view of the geometry of the needle cannula, the crimping pad and the crimping tool. It will also be appreciated that other techniques of metal forming may be employed and still practice aspects of the invention.

Once the proximal end of the cannula is properly positioned, the crimp tool is moved into the groove, thereby deforming the needle cannula. The tool radius is preferably less than the pad radius. Further, the tool is shifted proximally with respect to the groove. Consequently, the seal is formed at the very proximal end of the needle cannula substantially simultaneously with the formation of the hook shape. Preferably, the seal point of the crimp is disposed in a region between the very proximal end of the needle cannula and the midpoint of the hook-shape. The crimp design is selected to minimize stress in the initial bend area while providing a good mechanical geometry for securement by the adhesive. It will be appreciated that the die may be moved instead of the pin, or both the die and the pin may be moved, or the die, the pin and the needle cannula may be moved together to achieve the desired crimping and mechanical interlock.

Once the crimp and the hook-shaped member are formed, the hook is moved into the hub. Specifically, the hub is slipped along the cannula until the hook-shaped member is disposed in the glue well. An adhesive, such as a UV curable adhesive, is then applied to the glue well. The crimp prevents the glue from running into the cannula. Once in place, the UV curable adhesive is then cured with UV light.

Desirably, the height of the hook-shaped member is selected up to the maximum that would fit within the needle hub. The thickness of the cannula after crimping at the seal point is preferably less than or equal to twice the thickness of the cannula wall.

In certain applications, other mechanical interlocks may be formed to secure the cannula to the hub. For example, the crimping process may be employed to form a seal in the needle, but without a hook shape. The crimped portion of the needle cannula would then have a flattened oval shape. The oval would extend beyond the outer diameter of the undeformed cannula, at least in one dimension. This discontinuity on the needle shape could serve as a mechanical interlock to engage the needle hub body. Alternatively, the surface of the needle could be modified to have an irregular surface, such as a ribbed pattern, threads or fenestrations, that could be more readily secured to the needle hub body. Further, the needle cannula could be split, like a cotter pin, to provide better engagement with the needle hub. In certain such applications, it may be desirable to crimp the cannula distal of the mechanical interlock to prevent adhesive, if used, from flowing through the needle cannula during manufacture. Alternatively, a plug may be provided to prevent adhesive flow.

The preceding description is exemplary rather than limiting in nature. Variations and modifications to the disclosed examples may become apparent to those skilled in the art that do not necessarily depart from the purview and spirit of this invention. For example, implementations of the invention may be employed with other IV catheters introducers, both including safety engineered catheter introducers and conventional catheter introducers.

I claim:

1. A method of forming a needle assembly comprising:
   providing a cannula having a sharp distal end and a proximal end;
   crimping the proximal end to seal the proximal end;
   inserting the cannula into a needle hub such that the proximal end of the cannula is disposed in a glue well of the needle hub;
   inserting glue into the glue well; and
   curing the glue.

2. The method of claim 1 wherein the needle hub includes a neck having a profile substantially matching the profile of the cannula, and wherein the step of inserting the cannula into the needle hub includes positioning the cannula in the neck in a snug fit.

3. The method of claim 1 further comprising forming the proximal end of the cannula into a hook shape, wherein the step of crimping and the step of forming the hook are performed virtually simultaneously, wherein the crimp is formed by pressing a crimp pin onto the proximal end of the cannula, wherein the crimp is formed by pressing the proximal end of the cannula into a die, wherein the crimp pin is pressed into the proximal end of the cannula as the proximal end of the cannula is pressed into the die.

4. A method of forming a needle assembly comprising:
   providing a needle cannula having a distal end and a proximal end;
   inserting the needle cannula into a needle hub;
   extending the proximal end of the needle cannula beyond the needle hub;
   crimping the proximal end of the needle cannula such that it is sealed and formed into a mechanical interlock at the proximal end;
   displacing the cannula distally such that the mechanical interlock is disposed within a glue well in the needle hub;
   inserting glue into the glue well; and
   curing the glue with UV light.

5. The method of claim 4 further comprising lubricating the needle before inserting the needle cannula into the needle hub.

6. The method of claim 4 wherein the mechanical interlock is a hook and crimping the needle comprises:
   disposing the proximal end of the needle cannula along a crimping pad; and
   moving a crimping tool towards the needle cannula such that the tool forces the cannula onto the pad.

7. The method of claim 6 wherein the crimping tool is a crimping pin, and wherein the crimping pin is moved in a straight line towards the needle cannula.

8. The method of claim 7 in which the crimping pin is moved exclusively in a direction perpendicular to the axis of the needle cannula.

9. The method of claim 7 in which the crimping pin is moved in a direction at a selected angle with respect to the axis of the needle cannula.

10. The method of claim 7 in which the crimping pin is displaced in an arcuate path toward the crimping pad.

11. The method of claim 7 in which a groove is disposed in the crimping pad.

12. The method of claim 11 in which the crimping pin deforms the needle cannula into the groove.

13. The method of claim 12 in which the crimping pin moves with respect to the crimping pad in a path that is either in a direction perpendicular to the axis of the needle cannula, in a direction at a selected angle with respect to the axis of the needle cannula, arcuate toward the crimping pad or a combination of these paths.

14. The method of claim 12 in which the axis of the crimping pin is offset from the axis of the groove.

15. The method of claim 14 in which the axis of the crimping pin is offset proximally with respect to the axis of the groove.

* * * * *